United States Patent
Guillemont et al.

(10) Patent No.: US 8,618,100 B2
(45) Date of Patent: Dec. 31, 2013

(54) COMPOUNDS WITH ANTIBACTERIAL ACTIVITY AGAINST CLOSTRIDIUM

(75) Inventors: Jerome Emile Georges Guillemont, Ande (FR); Pierre Jean-Marie Bernard Raboisson, Rosieres (BE); Nacer Lounis, Wemmel (BE)

(73) Assignee: Elanco Animal Health Ireland Limited, Indianapolis, IN (US)

( * ) Notice: Subject to any disclaimer, the term of this patent is extended or adjusted under 35 U.S.C. 154(b) by 0 days.

(21) Appl. No.: 13/809,238

(22) PCT Filed: Aug. 4, 2011

(86) PCT No.: PCT/EP2011/063434
§ 371 (c)(1),
(2), (4) Date: Jan. 9, 2013

(87) PCT Pub. No.: WO2012/017030
PCT Pub. Date: Feb. 9, 2012

(65) Prior Publication Data
US 2013/0109694 A1     May 2, 2013

(30) Foreign Application Priority Data
Aug. 4, 2010  (EP) .................................... 10171842

(51) Int. Cl.
*A61K 31/53*   (2006.01)
*C07D 403/00*  (2006.01)

(52) U.S. Cl.
USPC ......................................... 514/245; 544/212

(58) Field of Classification Search
None
See application file for complete search history.

(56) References Cited

FOREIGN PATENT DOCUMENTS

| WO | 2008/039639 A2 | 4/2008 |
|---|---|---|
| WO | 2008/039640 A2 | 4/2008 |
| WO | 2008/039642 A2 | 4/2008 |
| WO | WO 2008039640 A2 * | 4/2008 |

OTHER PUBLICATIONS

Fighting the Impact of Antibiotic-Resistant Bacteria, FDA Consumer Health Information, 2013.*
Jarvest, R L, et al., "Optimisation of aryl substitution leading to potent methionyl tRNA synthetase inhibitors with excellent gram-positive antibacterial activity," Bioorganic and Medicinal Chemistry Letters, vol. 13, No. 4, pp. 665-668 (2003).
Jarvest, R L, et al., "Definition of the heterocyclic pharmacophore of bacterial methionyl tRNA synthetase inhibitors: potent antibacterially active non-quinolone analogues," Bioorganic & Medicinal Chemistry Letters Pergamon Elsevier Science GB, vol. 14, No. 15, pp. 3937-3941 (2004).
Lubbers, T., et al., "Design, synthesis, and structure-activity relationship studies of ATP analogues as DNA gyrase inhibitors", Bioorganic & Medicinal Chemistry, Letters Pergamon Elsevier Science GB, vol. 18, No. 8, pp. 821-826 (2008).
Vu, Chi B., et al., "Novel diamino derivatives of [1, 2, 4] triazolo[1, 5-a] [1, 3, 5] triazine as potent and selective adenosine A(2a) receptor antagonists", Journal of Medicinal Chemistry, vol. 48, No. 6, pp. 2009-2018 (2005).

* cited by examiner

*Primary Examiner* — Brandon Fetterolf
*Assistant Examiner* — Daniel M Podgorski
(74) *Attorney, Agent, or Firm* — James J. Sales

(57) ABSTRACT

The present invention is related to novel compounds of formula (I) having antibacterial activity against *Clostridium* bacteria, in particular *Clostridium perfringens*, pharmaceutical compositions comprising these compounds, and chemical processes for preparing these compounds.

15 Claims, No Drawings

COMPOUNDS WITH ANTIBACTERIAL ACTIVITY AGAINST *CLOSTRIDIUM*

This application claims priority to PCT/EP2011/063434 filed on Aug. 4, 2011, and EP10171842.7 filed on Aug. 4, 2010.

The present invention is related to novel compounds of formula (I) having antibacterial activity against *Clostridium* bacteria, in particular *Clostridium perfringens*, pharmaceutical compositions comprising these compounds, and chemical processes for preparing these compounds.

*Clostridium* is a genus of spore forming Gram-positive bacteria that grow under anaerobic conditions comprising more than 100 species. There are four main species responsible for diseases in humans and other warm-blooded animals: *C. botulinum* an organism producing a toxin in food or wounds that causes botulism; *C. difficile* that can cause pseudomembraneous colitis, toxic megacolon and antibiotic associated diarrheas; *C. tetani* which is the causative organism of tetanus; and *C. perfringens*.

*C. perfringens* is ubiquitous in the environment and is found in soil, dust, raw ingredients such as spices used in food processing, and in the intestines of humans and animals. It produces over 15 different toxins and infections due to *C. perfringens* can cause *C. perfringens* type A food poisoning, enterotoxemia, necrotizing enteritis, and gas gangrene. In the poultry industry, *C. perfringens* infections can cause gut health problems in broiler flocks with significant negative economical consequences. Since the use of antibiotics in the food industry is highly regulated there is a need for alternative antibacterial compounds.

WO-2008/039640 discloses the compound 5-[3-((R)(+)-6,8-dibromo-chroman-4-ylamino)-propylamino]-4H-thieno[3,2-b]pyridine-7-one, which is also known as REP3123, and its antibacterial activity against *Clostridium difficile*.

In vitro tests of the antibacterial activity of the REP3123 compound demonstrate that said compound is active against bacteria of the *Clostridium* genus however REP3123 also has antibacterial activity against a wide variety of bacteria that are present in the gut. Such a broad-spectrum antibacterial activity against Gram positive bacteria has a negative effect on the gut flora. Hence there is a need for antibacterial compounds with activity against bacteria of the *Clostridium* genus that have a narrow-spectrum activity against Gram positive bacteria and concomitantly no negative effect on the gut flora.

The present invention relates to a compound of formula (I)

(I)

including any stereochemically isomeric form and tautomer thereof wherein $R^1$ and $R^2$ are each independently selected from hydrogen, halo, hydroxy, $C_{1-6}$alkyl, polyhalo$C_{1-6}$alkyl, $C_{1-6}$alkyloxy, or polyhalo$C_{1-6}$alkyloxy;

$R^3$ is hydroxy, amino, mono- or di($C_{1-4}$alkyl)amino;

$R^4$ is hydrogen or $C_{1-4}$alkyl;

X is nitrogen or $CR^5$ wherein $R^5$ is hydrogen, halo or $C_{1-4}$alkyl;

provided that when $R^3$ is hydroxy than X represents CH and $R^4$ represents hydrogen;

or a pharmaceutically acceptable acid addition salt thereof, or a solvate thereof.

The proviso is intented to exclude compounds that have little or no antibacterial activity against bacteria of the *Clostridium* genus.

As used in the foregoing definitions:

halo is generic to fluoro, chloro, bromo and iodo;

$C_{1-4}$alkyl defines straight and branched chain saturated hydrocarbon radicals having from 1 to 4 carbon atoms such as, for example, methyl, ethyl, propyl, butyl, 1-methyl-ethyl, 2-methylpropyl and the like;

$C_{1-6}$alkyl is meant to include $C_{1-4}$alkyl and the higher homologues thereof having 5 or 6 carbon atoms, such as, for example, 2-methylbutyl, pentyl, hexyl and the like;

polyhalo$C_{1-6}$alkyl is defined as polyhalosubstituted $C_{1-6}$alkyl, in particular $C_{1-4}$alkyl (as hereinabove defined) substituted with 2 to 6 halogen atoms such as difluoromethyl, trifluoromethyl, trifluoroethyl, and the like.

The term "stereochemically isomeric forms" as used hereinbefore defines all the possible isomeric forms which the compounds of formula (I) may possess. Unless otherwise mentioned or indicated, the chemical designation of compounds denotes the mixture of all possible stereochemically isomeric forms, said mixtures containing all diastereomers and enantiomers of the basic molecular structure. More in particular, stereogenic centers may have the R- or S-configuration; substituents on bivalent cyclic (partially) saturated radicals may have either the cis- or trans-configuration. Stereochemically isomeric forms of the compounds of formula (I) are obviously intended to be embraced within the scope of this invention.

The absolute stereochemical configuration of the compounds of formula (I) and of the intermediates used in their preparation may easily be determined by those skilled in the art while using well-known methods such as, for example, X-ray diffraction.

Some of the compounds of formula (I) may also exist in their tautomeric form. Such forms although not explicitly indicated in the above formula are intended to be included within the scope of the present invention. For instance for compounds of formula (I) wherein $R^3$ represents hydroxy, the corresponding keto-form may be the mainly populated tautomer.

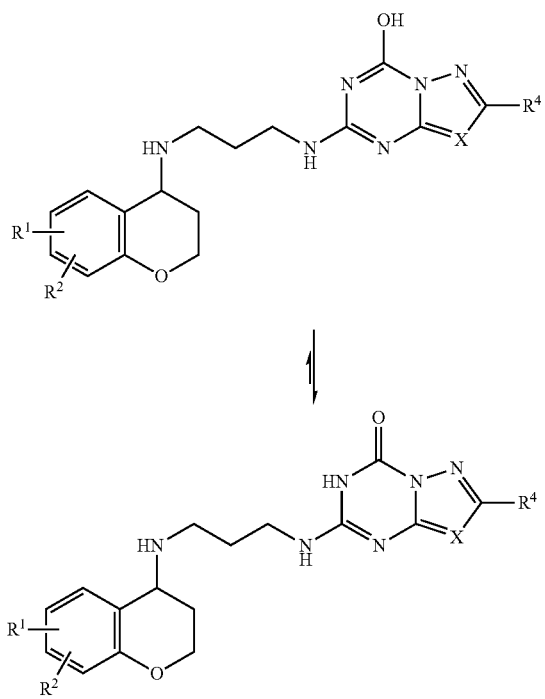

Furthermore, some compounds of formula (I) and some of the intermediates used in their preparation may exhibit polymorphism. It is to be understood that the present invention encompasses any polymorphic forms possessing properties useful in the treatment of the conditions noted hereinabove.

The pharmaceutically acceptable acid addition salts as mentioned hereinabove are meant to comprise the therapeutically active non-toxic acid addition salt forms that the compounds of formula (I) are able to form. These pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids.

Conversely said salt forms can be converted by treatment with an appropriate base into the free base form.

The compounds of formula (I) may exist in both unsolvated and solvated forms. The term 'solvate' is used herein to describe a molecular association comprising a compound of the invention and one or more pharmaceutically acceptable solvent molecules, e.g. water or ethanol. The term 'hydrate' is used when said solvent is water.

The compounds of formula (I) have at least one asymmetric carbon atoms as illustrated below wherein the asymmetric carbon atoms are identified by a *.

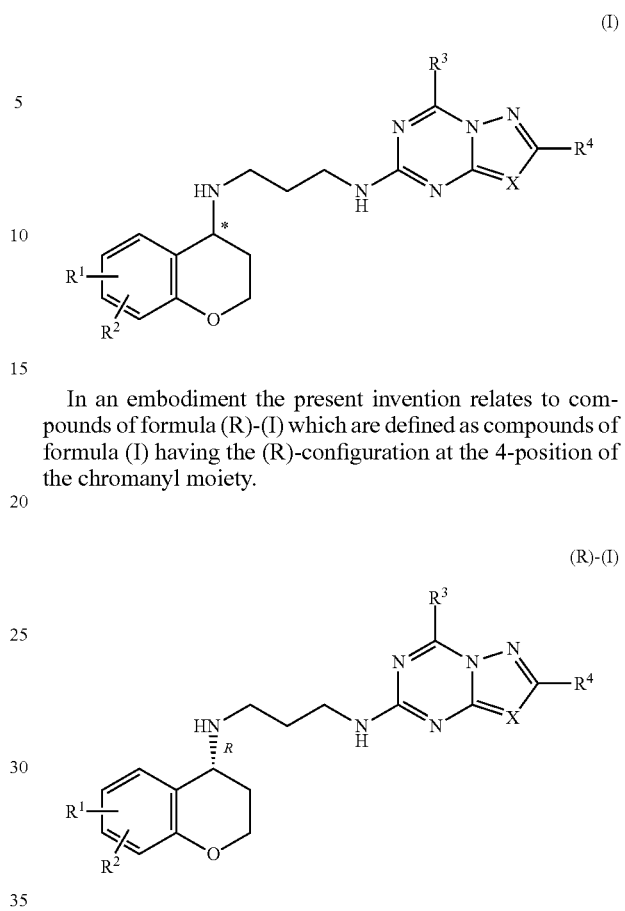

In an embodiment the present invention relates to compounds of formula (R)-(I) which are defined as compounds of formula (I) having the (R)-configuration at the 4-position of the chromanyl moiety.

Interesting compounds of formula (I) are those compounds of formula (I) wherein one or more of the following restrictions apply:
a) $R^1$ and $R^2$ are each halo; or
b) $R^1$ and $R^2$ are each bromo and are located at the 6- and 8-position of the chromanyl moiety; or
c) $R^3$ is hydroxy; or
d) $R^3$ is amino; or
e) $R^3$ is methylamino; or
f) $R^4$ is hydrogen; or
g) $R^4$ is methyl; or
h) X is nitrogen; or
i) X is $CR^5$ wherein $R^5$ represents hydrogen; or
j) X is $CR^5$ wherein $R^5$ represents halo, in particular chloro.

A first group of compounds are those compounds of formula (R)-(I) wherein $R^1$ and $R^2$ are each bromo and are located at the 6- and 8-position of the chromanyl moiety and wherein $R^3$ represents hydroxy.

A second group of compounds are those compounds of formula (R)-(I) wherein X represents nitrogen, $R^1$ and $R^2$ are each bromo and are located at the 6- and 8-position of the chromanyl moiety and wherein $R^3$ represents hydroxy.

A third group of compounds are those compounds of formula (R)-(I) wherein $R^1$ and $R^2$ are each bromo and are located at the 6- and 8-position of the chromanyl moiety and wherein $R^3$ represents amino.

Compounds of formula (I) can be prepared by reductively N-alkylating an intermediate an intermediate of formula (II) with an intermediate of formula (III), following art-known reductive N-alkylation procedures.

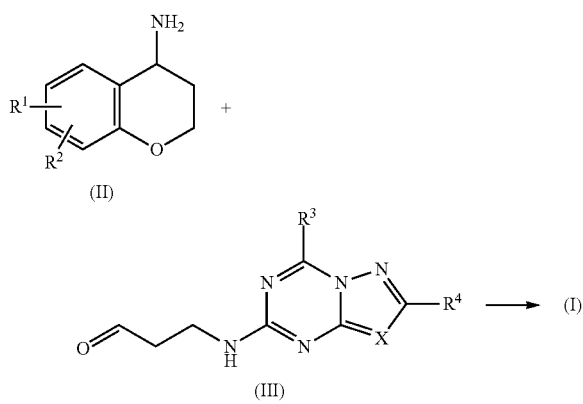

Said reductive N-alkylation can be performed in a reaction-inert solvent such as, for example, dichloromethane, THF, toluene or a mixture thereof, and in the presence of a reducing agent such as, for example, a borohydride, e.g. sodium borohydride, sodium cyanoborohydride or triacetoxy borohydride. It may also be convenient to use hydrogen as a reducing agent in combination with a suitable catalyst such as, for example, palladium-on-charcoal or platinum-on-charcoal. In case hydrogen is used as reducing agent, it may be advantageous to add a dehydrating agent to the reaction mixture such as, for example, aluminium tert-butoxide. In order to prevent the undesired further hydrogenation of certain functional groups in the reactants and the reaction products, it may also be advantageous to add an appropriate catalyst-poison to the reaction mixture, e.g., thiophene or quinoline-sulphur. To enhance the rate of the reaction, the temperature may be elevated in a range between room temperature and the reflux temperature of the reaction mixture and optionally the pressure of the hydrogen gas may be raised.

When compounds of formula (I) wherein $R^3$ represents amino or mono-($C_{1-4}$alkyl)-amino are prepared using the above described N-alkylation method, it may be appropriate to protect said amine functionality. Protecting groups for amine functionalities are art-known and are removed after the N-alkylation procedure.

Also compounds of formula (I) wherein $R^3$ represents hydroxy can be prepared using the above described N-alkylation procedure whereby the hydroxy functionality is protected by art-known protecting groups.

Compounds of formula (I-a), defined as compounds of formula (I) wherein $R^3$ represents hydroxy, can be prepared by hydrolysing intermediates of formula (IV) under basic conditions. Intermediates of formula (IV) can be prepared in accordance with the general N-alkylation procedure as described above.

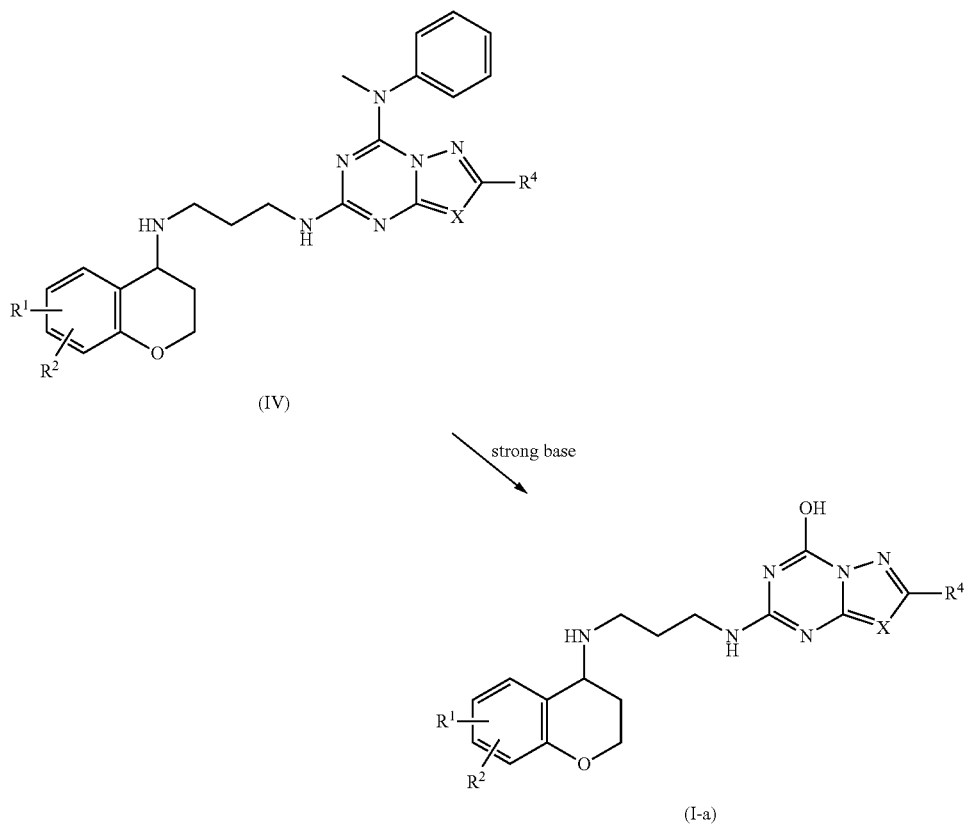

The starting materials and some of the intermediates are known compounds and are commercially available or may be prepared according to conventional reaction procedures generally known in the art.

The compounds of formula (I) as prepared in the hereinabove described processes may be synthesized in the form of racemic mixtures of enantiomers which can be separated from one another following art-known resolution procedures. Those compounds of formula (I) that are obtained in racemic form may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

The compounds of formula (I), including any stereochemically isomeric forms and tautomers thereof, and the pharmaceutically acceptable salts thereof possess antibacterial activity, in particular against bacteria of the *Clostridium* genus, more particulary *Clostridium perfringens*, as demonstrated in the Pharmacological Examples.

Therefore the present invention also relates to compounds of formula (I) for use as a medicine especially for use in the treatment of bacterial infections, in particular *Clostridium* based infections, more particularly *Clostridium perfringens* based infections. Subsequently the present compounds may be used for the manufacture of a medicine for treatment of bacterial infections, in particular *Clostridium* based infections, more particularly *Clostridium perfringens* based infections.

Further, the present invention provides a method of treatment of a bacterial infection, in particular *Clostridium* based infections, more particularly *Clostridium perfringens* based infections, in a warm-blooded subject which comprises administering to the warm-blooded subject in need of such treatment a therapeutically effective amount of a compound of formula (I) or a pharmaceutically acceptable salt thereof.

*Clostridium perfringens* based infections are e.g. *C. perfringens* type A food poisoning, enterotoxemia, necrotizing enteritis, and gas gangrene.

The term "treating" and "treatment", as used herein, refers to curative, palliative and prophylactic treatment, including reversing, alleviating, inhibiting the progress of, or preventing the disease, disorder or condition to which such term applies, or one or more symptoms of such disease, disorder or condition.

Warm-blooded animals as used throughout this text include both human and non-human animals such as farm animals (e.g. sheep, cattle, swine, goats or horses), domestic animals (e.g. dogs, cats, or cavias) as well as wild animals held in captivity and birds (e.g. poultry).

Additionally the present invention provides pharmaceutical compositions comprising at least one pharmaceutically acceptable carrier and a therapeutically effective amount of a compound of formula (I).

The term "therapeutically effective amount of a compound of formula (I)" as used herein, means that amount of compound of formula (I) that elicits the biological or medicinal response in the warm-blooded animal that is being sought by the physician or veterinarian, which includes alleviation of the symptoms of the condition being treated. The therapeutically effective amount can be determined using routine optimization techniques and is dependent upon the particular condition to be treated, the condition of the warm-blooded animal, the route of administration, the formulation, and the judgment of the practitioner and other factors evident to those skilled in the art. A therapeutically effective amount may be achieved by multiple dosing.

Additionally the present invention provides pharmaceutical compositions comprising at least one pharmaceutically acceptable carrier and a therapeutically effective amount of a compound of formula (I).

For use in warm-blooded animals, including humans, the compounds of formula (I) can be administered alone, but will generally be administered in admixture with a pharmaceutically or veterinary acceptable diluent or carrier selected with regard to the intended route of administration and standard pharmaceutical practice. For example, they can be administered orally, including sublingually, in the form of tablets containing such excipients as starch or lactose, or in capsules or ovules either alone or in admixture with excipients, or in the form of elixirs, solutions or suspensions containing flavouring or colouring agents. The compounds of formula (I) could be incorporated into capsules, tablets or boluses for targeting the colon or duodenum via delayed dissolution of said capsules, tablets or boluses for a particular time following oral administration. The compounds of formula (I) can be injected parenterally, for example, intravenously, intramuscularly or subcutaneously. For parenteral administration, they are best used in the form of a sterile aqueous solution or suspension that may contain other substances, for example, enough salt or glucose to make the solution isotonic with blood. The compounds of formula (I) can be administered topically, in the form of sterile creams, gels, pour-on or spot-on formulations, suspensions, lotions, ointments, dusting powders, sprays, drug-incorporated dressings or via a skin patch. For example the compounds of formula (I) can be incorporated into a cream consisting of an aqueous or oily emulsion of polyethylene glycols or liquid paraffin, or they can be incorporated into an ointment consisting of a white wax soft paraffin base, or as hydrogel with cellulose or polyacrylate derivatives or other viscosity modifiers, or as a dry powder or liquid spray or aerosol with butane/propane, HFA or CFC propellants, or as a drug-incorporated dressing either as a tulle dressing, with white soft paraffin or polyethylene glycols impregnated gauze dressings or with hydrogel, hydrocolloid, alginate or film dressings. The compounds of formula (I) could also be administered intra-ocularly as an eye drop with appropriate buffers, viscosity modifiers (e.g. cellulose derivatives), preservatives (e.g. benzalkonium chloride (BZK)) and agents to adjust tenicity (e.g. sodium chloride). Such formulation techniques are well-known in the art. All such formulations may also contain appropriate stabilizers and preservatives.

For veterinary use, compounds can be administered as a suitably acceptable formulation in accordance with normal veterinary practice and the veterinarian will determine the dosing regimen and route of administration which will be most appropriate for a particular animal.

For topical application dip, spray, powder, dust, pour-on, spot-on, emulsifiable concentrate, jetting fluid, shampoos, collar, tag or harness may be used. Such formulations are prepared in a conventional manner in accordance with standard veterinary and pharmaceutical practice. Thus capsules, boluses or tablets may be prepared by mixing the active ingredient with a suitable finely divided diluent or carrier, additionally containing a disintegrating agent and/or binder such as starch, lactose, talc, or magnesium stearate. A drench formulation may be prepared by dispersing the active ingredients in an aqueous solution together with dispersing or wetting agents and injectable formulations may be prepared in the form of a sterile solution or emulsion. Pour-on or spot-on formulations may be prepared by dissolving the active ingredients in an acceptable liquid carrier vehicle, such as butyl digol, liquid paraffin or non-volatile ester with or without addition of a volatile component such as isopropanol.

Alternatively, pour-on, spot-on or spray formulations can be prepared by encapsulation to leave a residue of active agent on the surface of the animal. These formulations will vary with regard to the weight of active compound depending on the species of host animal to be treated, the severity and type of infection and type and body weight of the host. The formulations comprising a compound of formula (I) may be administered continuously, particularly for prophylaxis by known methods.

As an alternative the combinations may be administered with the animal feedstuff and for this purpose a concentrated feed additive or premix may be prepared for mixing with the normal animal feed.

For human use the compounds of formula (I) are administered as a pharmaceutically acceptable formulation in accordance with normal medical practice.

Those skilled in the treatment of bacterial infections, in particular *Clostridium* infections, will easily determine the therapeutically effective amount of a compound of formula (I) from the test results presented hereinafter. In general it is contemplated that a therapeutically effective dose will be from about 0.1 mg/kg to about 20 mg/kg of body weight, more preferably from about 1 mg/kg to about 10 mg/kg of body weight of the warm-blooded animal to be treated. It may be appropriate to administer the therapeutically effective dose in the form of two or more sub-doses at appropriate intervals throughout the day.

The exact dosage and frequency of administration depends on the particular compound of formula (I) used, the particular condition being treated, the severity of the condition being treated, the age, weight and general physical condition of the particular warm-blooded animal as well as the other medication, the warm-blooded may be taking, as is well known to those skilled in the art. Furthermore, said effective daily amount may be lowered or increased depending on the response of the treated animal and/or depending on the evaluation of the physician or veterinarian prescribing the compounds of the instant invention. The effective daily amount ranges mentioned hereinabove are therefore only guidelines.

EXPERIMENTAL PART

"DMF" is defined as N,N-dimethylformamide, "CH$_2$Cl$_2$" is defined as dichloromethane, "MeOH" is defined as methanol, "EtOH" is defined as ethanol, "TEA" is defined as triethylamine, "DPPA" is defined as phosphorazidic acid diphanyl ester, "DBU" is defined as 2,3,4,6,7,8,9,10-octahydropyrimido[1,2-a]azepine, "NaBH(OAc)$_3$" is defined as sodium triacetoxyborohydride, "MgSO$_4$" is defined as magnesium sulfate, "POCl$_3$" is defined as phosphoric trichloride, "Na$_2$SO$_3$" is defined as sodium sulfite, "CH$_3$NH$_2$" is defined as methanamine, "NaHCO$_3$" is defined as sodium bicarbonate, "CHCl$_3$" is defined as trichloromethane, "Na$_2$SO$_4$" is defined as sodium sulfate, "NH$_4$OH" is defined as ammonium hydroxide, "H$_2$SO$_4$" is defined as sulfuric acid, "NCS" is defined as 1-chloro-2,5-pyrrolidinedione, "NaOH" is defined as sodium hydroxide and "THF" is defined as tetrahydrofuran.

For a number of compounds, melting points (mp.) were determined with a WRS-2A melting point apparatus that was purchased from Shanghai Precision and Scientific Instrument Co. Ltd. Melting points were measured with a linear heating up rate of 0.2-5.0° C./minute. The reported values are melt ranges. The maximum temperature was 300° C.

$^1$H NMR

For a number of compounds, $^1$H NMR spectra were recorded on a Bruker DPX-300, or on a Bruker DPX-400 spectrometer with standard pulse sequences, operating at 300 MHz and 400 MHz respectively, using CHLOROFORM-d (deuterated chloroform, CDCl$_3$) or DMSO-d$_6$ (deuterated DMSO, dimethyl-d6 sulfoxide) as solvents. Chemical shifts (δ) are reported in parts per million (ppm) relative to tetramethylsilane (TMS), which was used as internal standard.

A. Synthesis of the Intermediates

Example A.1 a) Preparation of intermediate (1)

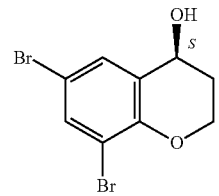

Formic acid (81 g) was added dropwise at 0° C. to TEA (1040 mmol). After stirring for 10 minutes, 6,8-dibromo-2,3-dihydro-4H-1-benzopyran-4-one (261 mmol) was added to the reaction mixture, followed by intermediate (14) (0.5 mmol) and DMF (300 ml) at 25° C. After the addition, the reaction mixture was stirred at 40° C. for 24 hours. Thin layer chromatography (petroleum ether/ethyl acetate=5/1) showed that the reaction was finished. The reaction mixture was quenched by the addition of water (1000 ml) at 0° C. The resulting reaction mixture was extracted with ethyl acetate (three times 1000 ml). The organic phase was washed with brine (500 ml), dried over Na$_2$SO$_4$ and concentrated to give the crude product. The crude product was washed with tert-butyl methyl ether to give 78 g of intermediate (1).

b) Preparation of intermediate (2)

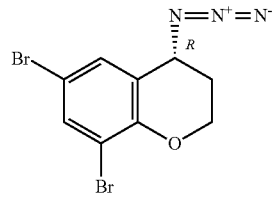

To a stirred solution of intermediate (1) (253 mmol) in THF (2000 ml) was added DPPA (334 mmol) at 25° C. After stirring for 15 minutes at 25° C., DBU (691 mmol) was added at 0° C. After the addition, the reaction mixture was stirred at room temperature for 12 hours. Thin layer chromatography (petroleum ether/ ethyl acetate=10:1) showed that the starting material was consumed completely. The reaction mixture was treated with water (1000 ml) and extracted with ethyl acetate (three times 1000 ml). The organic phase was washed with brine (1000 ml), dried over Na$_2$SO$_4$ and concentrated to give the crude product. The crude product was purified by silica gel chromatography (petroleum ether/ethyl acetate=50/1) to give 60.3 g of intermediate (2).

c) Preparation of intermediate (3)

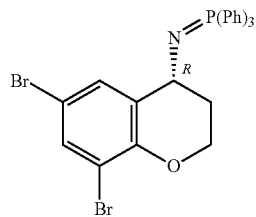

Triphenylphosphine (362 mmol) was added to the mixture of intermediate (2) (181 mmol) in H$_2$O (80 ml) and THF (800 ml) at 25° C. After the addition, the reaction mixture was stirred at 25° C. for 1 hour. Thin layer chromatography (petroleum ether/ethyl acetate=5/1) showed that the reaction was finished. The reaction mixture was concentrated and the residue was portioned between ethyl acetate (1000 ml) and H$_2$O (1000 ml). After separated, the aqueous phase was extracted with ethyl acetate (500 ml). The organic phase was washed with brine (1000 ml), dried over Na$_2$SO$_4$ and concentrated to give 150 g of intermediate (3).

d) Preparation of intermediate (4)

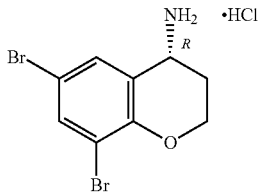

NH$_4$OH (180 ml) was added to the solution of intermediate (3) (181 mmol) in EtOH (1500 ml) at 0° C. The resulting reaction mixture was heated under reflux for 3 hours. Thin layer chromatography (CH$_2$Cl$_2$/MeOH=10/1) showed that the reaction was finished. The reaction mixture was evaporated to remove EtOH and the residue was acidified by the addition of 6N HCl to pH=2. The resulting mixture was filtered and the resulting solid was washed with ethyl acetate (500 ml) to give 40 g of intermediate (4).

Example A.2 a) Preparation of intermediate 5

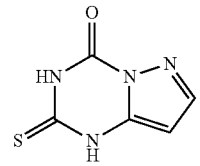

A mixture of N-[(1H-pyrazol-3-ylamino)thioxomethyl]-carbamic acid ethyl ester (514 mmol) in 2N aqueous NaOH (565 mmol) was stirred at 15° C. for 3 hours. Then the mixture was acidified with 2N H$_2$SO$_4$. The precipitate was filtered, washed with water (1000 ml) and tert-butyl methylether (500 ml). The resulting solid was dried under vacuum to give the product as a white solid, yielding 78 g of intermediate (5).

b) Preparation of intermediate (6)

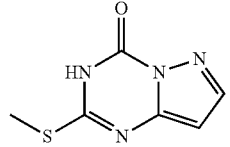

To a stirred suspension of intermediate (5) (464 mmol, 1 equivalent) in EtOH (1600 ml) was added dropwise aqueous 2N NaOH solution (480 ml, 2 equivalents), followed by iodomethane (511 mmol, 1.1 equivalents) at 0° C. After addition, the mixture was stirred at 15° C. for 2 hours. Thin Layer Chromatography (CH$_2$Cl$_2$/MeOH=10/1) showed the reaction was completed. The precipitate was filtered and then suspended in water (800 ml) and then acidified by 2N H$_2$SO$_4$. The suspension was stirred at 0° C. for 5 minutes. The precipitate was filtered and washed by cold water (900 ml). The resulting solid was dried in vacuum to yield 75 g of intermediate (6) as a white solid.

c) Preparation of intermediate (7)

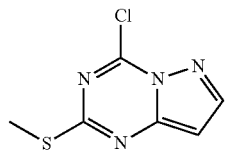

A mixture of intermediate (6) (374 mmol), N,N-dimethyl-4-pyridinamine (1.31 mmol) in POCl$_3$ (1500 ml) was heated to reflux for 2 hours at 100° C. After cooling to room temperature, the excess of POCl$_3$ was removed under vacuum and the resulting residue was dried for 2 hours. The crude product was used directly for next step without further purification, yielding 240 g of intermediate (7).

d) Preparation of intermediate (8)

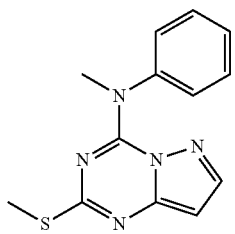

Intermediate (7) (374 mmol) was dissolved in dry CH$_2$Cl$_2$ (2000 ml), then N-methyl-benzenamine (285 ml) and TEA (355 ml) were added dropwise at 0° C. After stirring for 10 minutes, the mixture was allowed to warm up to room temperature and stirred overnight. Thin Layer Chromatography (CH$_2$Cl$_2$/MeOH=10/1) showed the reaction was complete. The reaction mixture was washed with water (600 ml) and brine (300 ml). The organic layer was dried over MgSO$_4$, filtered and concentrated to give the crude product, which was further washed by EtOH to give 82 g of intermediate (8).

e) Preparation of intermediate (9)

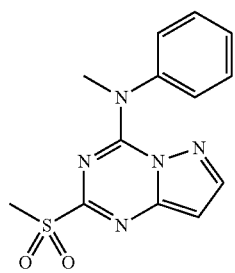

To a stirred solution of intermediate (8) (303 mmol) in CH$_2$Cl$_2$ (2000 ml) was added 3-chloroperoxybenzoic acid (1059 mmol) at 0° C. in portions. After the addition, the reaction mixture was stirred at 0° C. for 1 hour and then at 15° C. for 2 hours. Thin Layer Chromatography (petroleum ether/ethyl acetate=5/1) showed that the reaction was completed. The reaction mixture was washed by saturated Na$_2$SO$_3$ aqueous (four times with 600 ml) and then saturated NaHCO$_3$ aqueous was added until pH=7. The aqueous layer was extracted by CH$_2$Cl$_2$ (500 ml). The combined organic phases were washed with brine (800 ml), dried over Na$_2$SO$_4$ and concentrated to give the crude product. The crude product was washed by tert-butyl methylether (three times with 500 ml) to give 87 g of intermediate (9).

f) Preparation of intermediate (10)

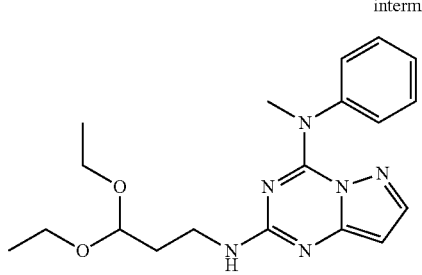

To a stirred solution of intermediate (9) (287 mmol) in CHCl$_3$ (2000 ml) was added 3,3-diethoxy-1-propanamine (474 mmol) at 0° C. in portions. After the addition, the reaction mixture was stirred at 0° C. for 1 hour and then at 15° C. for 2 hours. Thin Layer Chromatography (petroleum ether/ethyl acetate=5/1) showed that the reaction was completed. The reaction mixture was washed by saturated Na$_2$SO$_3$ aqueous (four times with 600 ml) and then saturated NaHCO$_3$ aqueous was added until pH=7. The aqueous layer was extracted by CH$_2$Cl$_2$ (500 ml). The combined organic phases were washed with brine (800 ml), dried over Na$_2$SO$_4$ and concentrated to give the crude product. The crude product was washed by tert-butyl methylether (three times 500 ml) to give 87 g of intermediate (10) (mp. 100.8-103.8° C.).

g) Preparation of intermediate (11)

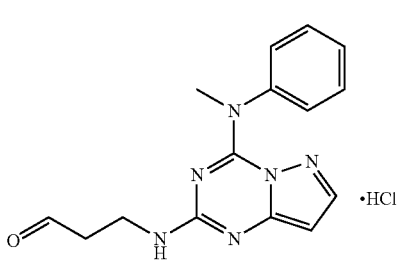

12N HCl (7.5 ml) was added to the solution of intermediate (10) (81 mmol) in THF (450 ml) below 20° C. After stirring for 5 minutes, the reaction mixture was stirred at 20° C. for 1 hour. Thin Layer Chromatography (CH$_2$Cl$_2$/MeOH=20/1) showed that the reaction was complete. Ethyl acetate (500 ml) was added. The reaction mixture was stirred for 30 minutes. The precipitate was filtered, washed with ethyl acetate and dried in vacuum to give 32 g of intermediate (11).

Example A.3

Preparation of intermediate (14)

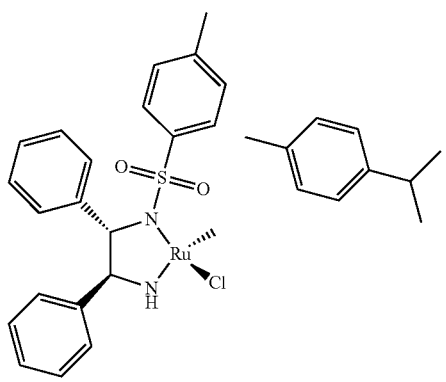

A mixture of N-[(1S,2S)-2-amino-1,2-diphenylethyl]-4-methyl-benzenesulfonamide (2.13 mmol), dichloro(p-cymene)ruthenium(II) dimer (2.13 mmol) and TEA (0.6 ml) in 2-propanol (21 ml) was stirred at 80° C. for 1 hour. After cooling to 20° C., the organic solution was concentrated under vacuum. The resulting solid was washed with water (10 ml) and dried under reduce pressure to give the crude product, which was further re-crystallized from methanol to give 0.37 g of the product as a bright orange solid intermediate (14).

B. Preparation of the Final Compounds

Example B.1 a) Preparation of intermediate (12)

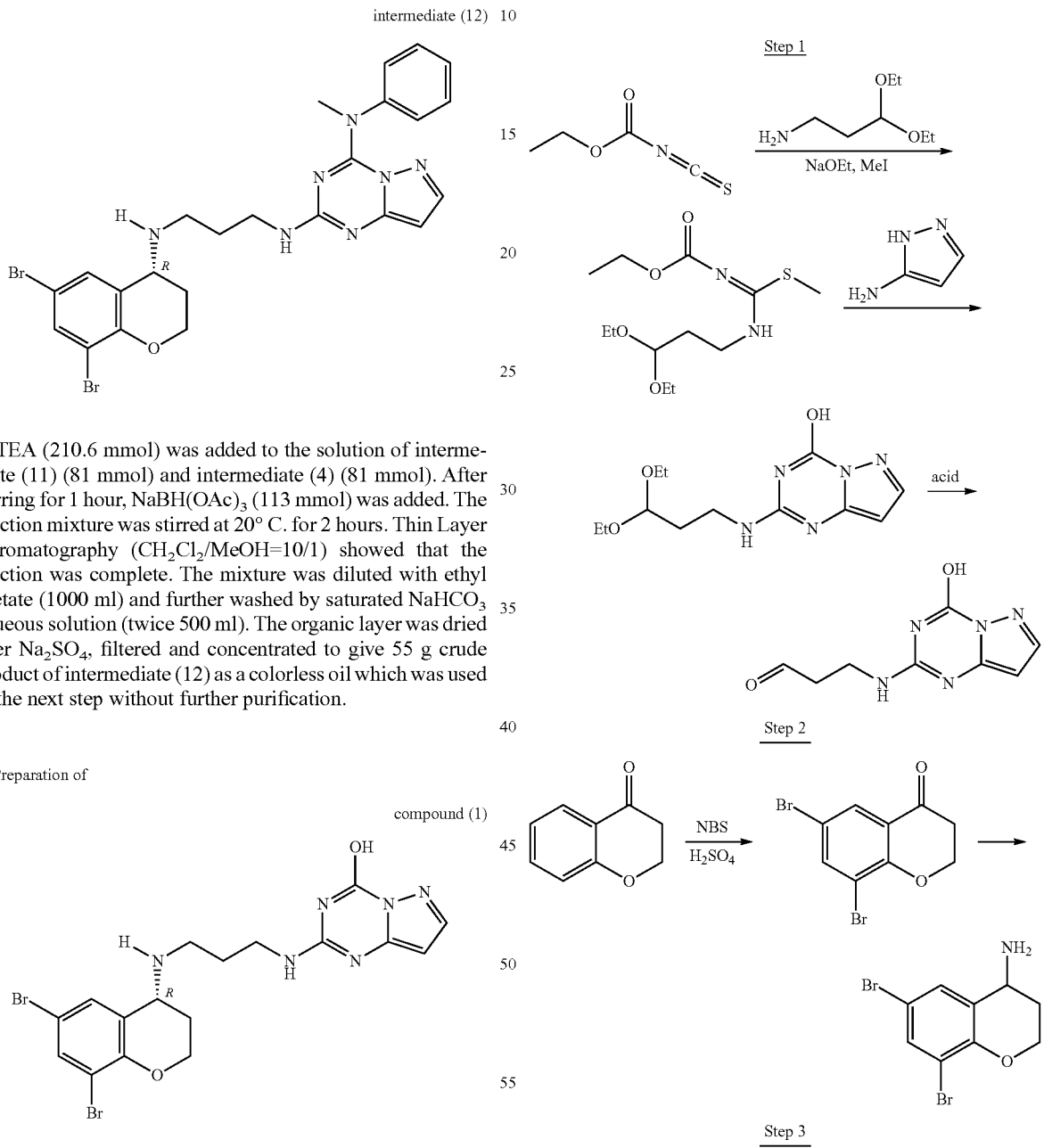

TEA (210.6 mmol) was added to the solution of intermediate (11) (81 mmol) and intermediate (4) (81 mmol). After stirring for 1 hour, NaBH(OAc)₃ (113 mmol) was added. The reaction mixture was stirred at 20° C. for 2 hours. Thin Layer Chromatography (CH₂Cl₂/MeOH=10/1) showed that the reaction was complete. The mixture was diluted with ethyl acetate (1000 ml) and further washed by saturated NaHCO₃ aqueous solution (twice 500 ml). The organic layer was dried over Na₂SO₄, filtered and concentrated to give 55 g crude product of intermediate (12) as a colorless oil which was used in the next step without further purification.

b) Preparation of compound (1)

To a stirred solution of intermediate (12) (6 mmol) in EtOH (100 ml) was added 5N NaOH (12 ml) dropwise at 0° C. After addition, the reaction mixture was heated to reflux for 3 hours at 85° C. Thin Layer Chromatography (CH₂Cl₂/MeOH=10/1) showed that the reaction was complete. EtOH was removed under reduced pressure and the residue was neutralized with saturated aqueous citric acid to pH=7. The mixture was added to a solution of water (50 ml) and ethyl acetate (100 ml). The precipitate was filtered, washed with acetonitrile (three times 50 ml) and dried in vacuum to give 1.8 g of compound (1).

Compound (5) was prepared using the same procedure by reacting intermediate (11) with (R)-6,8-dichloro-chroman-4-ylamine.

An alternative method for the preparation of compound (1) is depicted below.

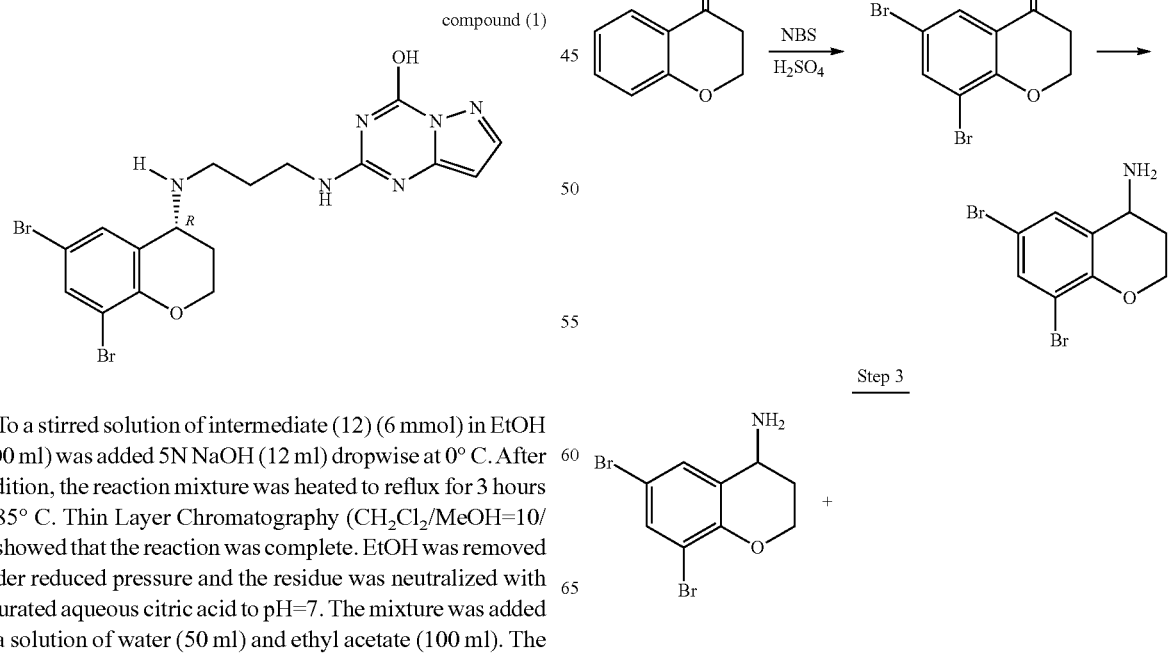

Example B.2

Preparation of

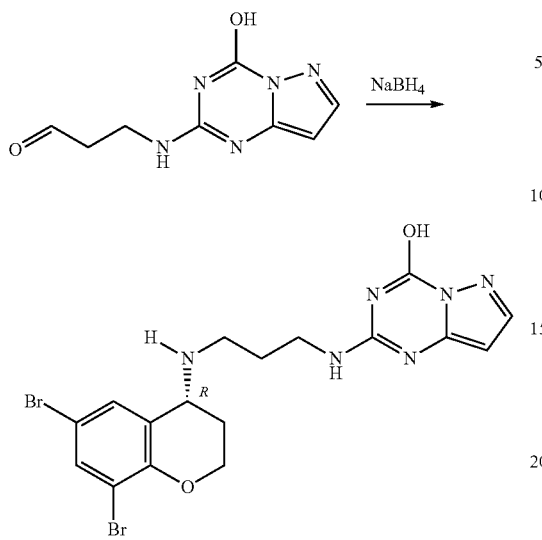

compound (2)

4M HCl in dioxane (30 ml) was added to the solution of compound (1) (3.6 mmol) in MeOH (10 ml) at 20° C. The mixture was stirred for 3 hours at 20° C. The solvent was removed under reduced pressure. The residue was dried in vacuum, yielding 1.62 g of compound (2) (mp.: 234.6-235.6° C.). Optical Rotation: $[\alpha]_{589}^{20}$=+10.67, 8.77 mg/ml, methanol.

$^1$H NMR (400 MHz, DMSO-$d_6$) δ ppm 1.86-2.07 (m, 2 H) 2.14-2.28 (m, 1 H) 2.30-2.44 (m, 1 H) 3.04 (br. s., 1 H) 3.17 (br. s., 1 H) 3.36-3.43 (m, 2 H) 4.34-4.43 (m, 1 H) 4.43-4.52 (m, 1 H) 4.52-4.60 (m, 1 H) 5.88 (d, J=2.0 Hz, 1 H) 7.11 (t, J=5.4 Hz, 1 H) 7.78 (d, J=1.6 Hz, 1 H) 7.81-7.89 (m, 2 H) 9.21 (br. s., 1 H) 9.32 (br. s., 1 H)

Example B.3 a) Preparation of

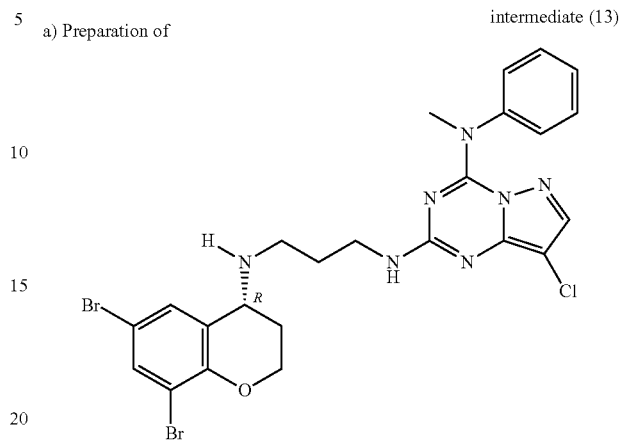

intermediate (13)

A solution of intermediate (12) (10.2 mmol) in DMF (300 ml) was stirred at 80° C. for 5 minutes. NCS (20.4 mmol) was added to the mixture under nitrogen atmosphere and the reaction was stirred for 3 hours. Then DMF was removed under reduced pressure. The residue was washed with tert-butyl methyl ether (three times 50 ml) and filtered. The solid was dried under reduced pressure, yielding 2.8 g of intermediate (13).

b) Preparation of

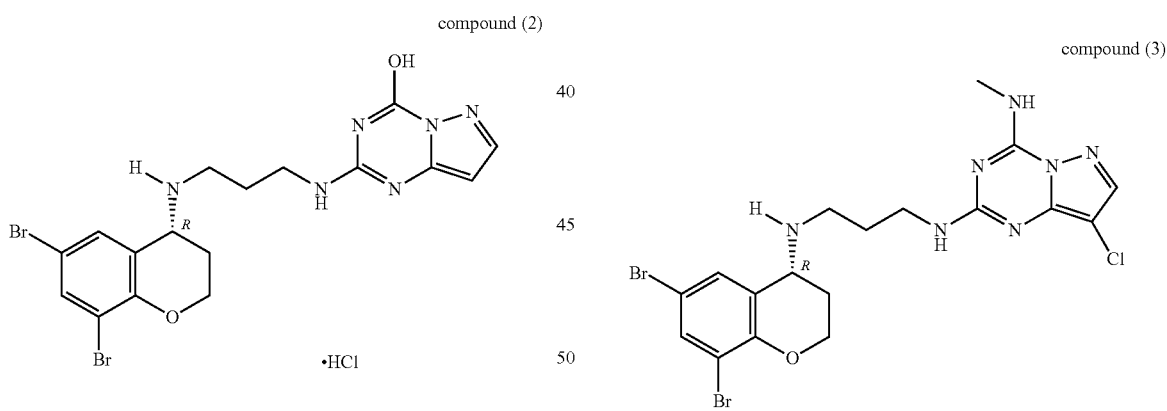

compound (3)

Intermediate (13) (0.97 mmol) and 2M $CH_3NH_2$ in THF (5 ml) was added to anhydrous EtOH (5 ml) at 20° C. The mixture was stirred at 150° C. under microwave for 4 hours. EtOH was removed under reduced pressure. The residue was purified with preparative high performance liquid chromatography (column: YMC, 250×20 mm, mobile phase: 20-50% $CH_3CN$(0.075% v/v $CF_3COOH$), flow rate: 25 ml/min, finished time: 15 minutes). The desired fraction was collected and evaporated. The aqueous solution was neutralized to pH=7 and concentrated. The solid was filtered and washed by water (three times 30 ml), yielding 0.065 g of compound (3) (mp.: 108.8-118.6° C.).

Example B.4

Preparation of

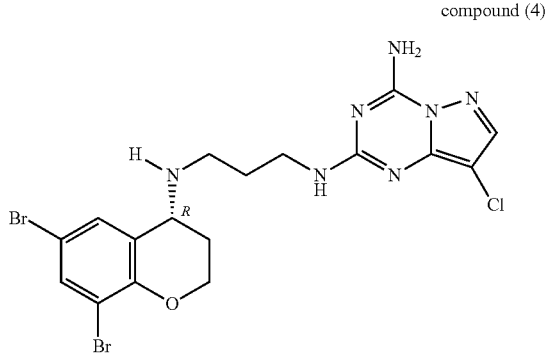

compound (4)

A mixture of intermediate (13) (0.97 mmol) and 2M NH$_3$ in MeOH (10 ml) was stirred at 125° C. under microwave for 3 hours. The mixture was concentrated under reduced pressure. The residue was purified with preparative high performance liquid chromatography (column: YMC, 250×20 mm, mobile phase: 30-60% CH$_3$CN (0.075% v/v CF$_3$COOH), flow rate: 25 ml/min, finished time: 15 minutes). The desired fraction was collected and evaporated. The aqueous solution was neutralized to pH=7 and concentrated. The resulting solid was filtrated and further washed by water (three times 30 ml). The product was dried under high vacuum, yielding 0.09 g of compound (4) (mp.: 78.7-94.1° C.).

Table 1 lists the compounds that were prepared according to one of the above Examples.

TABLE 1

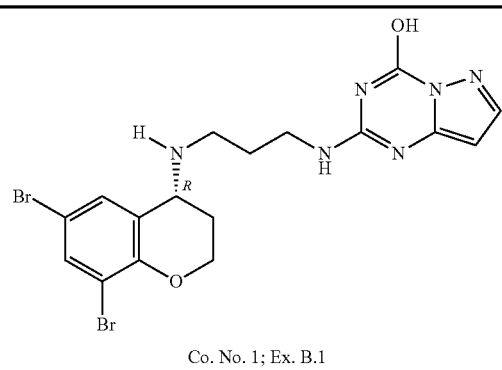

Co. No. 1; Ex. B.1

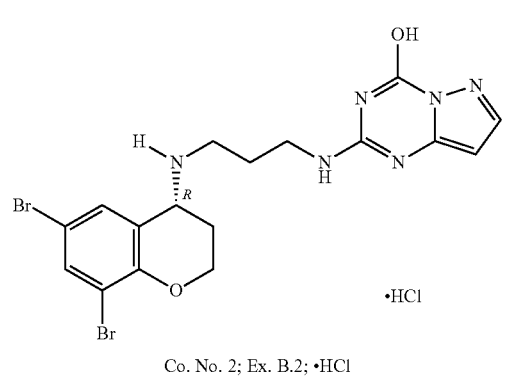

Co. No. 2; Ex. B.2; •HCl

TABLE 1-continued

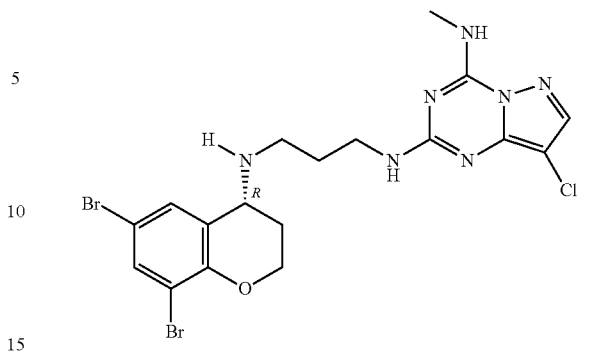

Co. No. 3; Ex. B.3

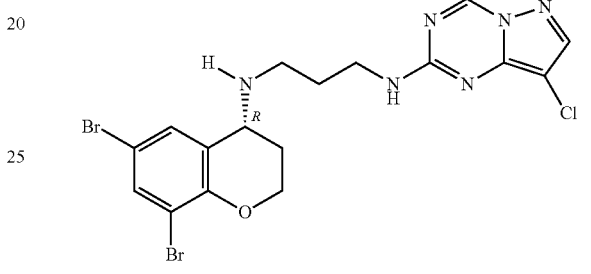

Co. No. 4; Ex. B.4

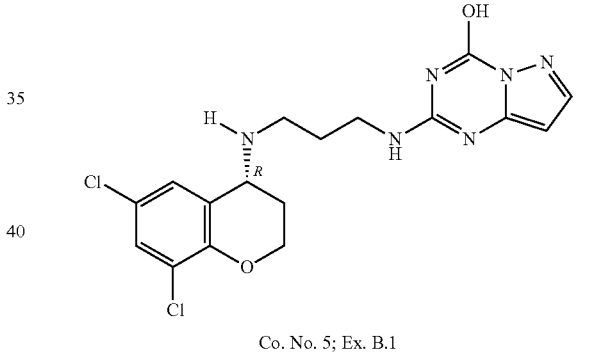

Co. No. 5; Ex. B.1

C. Analytical Part

C.1. LC-MS General Procedure A

General Procedure A

The HPLC measurement was performed using an Agilent 1100 module comprising a pump, a diode-array detector (DAD) (wavelength used 220 nm), a column heater and a column as specified in the respective methods below. Flow from the column was split to a Agilent MSD Series G1946C and G1956A. MS detector was configured with API-ES (atmospheric pressure electrospray ionization). Mass spectra were acquired by scanning from 100 to 1000. The capillary needle voltage was 2500 V for positive ionization mode and 3000 V for negative ionization mode. Fragmentation voltage was 50 V. Drying gas temperature was maintained at 350° C. at a flow of 10 l/min.

Method 1

In addition to general procedure A: Reversed phase HPLC was carried out on a YMC-Pack ODS-AQ, 50×2.0 mm 5 µm column with a flow rate of 0.8 ml/min. Two mobile phases (mobile phase A: water with 0.1% TFA; mobile phase B: acetonitrile with 0.05% TFA) were used. First, 100% A was hold for 1 minute. Then a gradient was applied to 40% A and 60% B in 4 minutes and hold for 2.5 minutes. Typical injection volumes of 2 µl were used. Oven temperature was 50° C. (MS polarity: positive)

Method 2

In addition to general procedure A: Reversed phase HPLC was carried out on a YMC-Pack ODS-AQ, 50×2.0 mm 5 µm column with a flow rate of 0.8 ml/min. Two mobile phases (mobile phase A: water with 0.1% TFA; mobile phase B: acetonitrile with 0.05 TFA) were used. First, 90% A and 10% B was hold for 0.8 minutes. Then a gradient was applied to 20% A and 80% B in 3.7 minutes and hold for 3 minutes. Typical injection volumes of 2 µl were used. Oven temperature was 50° C. (MS polarity: positive)

TABLE 2

Analytical data—Retention time ($R_t$ in minutes), $(MH)^+$ peak (of the free base), LC-MS procedure and melting points (m.p. is defined as melting point).

| Co. Nr. | $R_t$ | $(MH)^+$ | LC-MS Procedure |
|---|---|---|---|
| 1 | 4.16 | 499.0 | 1 |
| 2 | 4 | 468.9 | 1 |
| 3 | 3.39 | 545.9 | 2 |
| 4 | 3.25 | 531.9 | 2 |

D. Pharmacological Examples

D.1.1 In-vitro Method for Testing Compounds Against *C. perfringens*

Flat-bottom, sterile 96-well plastic microtiter plates were filled with 100 µl Brain heart infusion broth medium. Subsequently, stock solutions (100×final test concentration) of compounds were added in 2 µl volumes to a series of wells so as to allow evaluation of their effects on bacterial growth. Untreated control samples with and without inoculum were included in each microtiter plate. Approximately 50000 CFU per well of *Clostridium perfringens* (strain 56), in a volume of 100 μl in Brain heart infusion broth medium, was added to the wells. The cultures were incubated at 37° C. for 24 hours in an anaerobic jar. The optical density (OD) was read in a computer-controlled spectrophotometer (Envision) at a wavelength of 540 nm. The percentage growth inhibition achieved by the compounds was calculated according to standard methods and expressed as $IC_{90}$ (μg/ml) which defines the 90% inhibitory concentration for bacterial growth.

D.1.2 In-vitro Method for Testing Compounds for Anti-Bacterial Activity Against Strain *C. difficile*

Flat-bottom, sterile 96-well plastic microtiter plates were filled with 100 μl of Reinforced Clostridial broth medium. Subsequently, stock solutions (100×final test concentration) of compounds were added in 2 μl volumes to a series of wells so as to allow evaluation of their effects on bacterial growth. Untreated control samples with and without inoculum were included in each microtiter plate. Approximately 50000 CFU per well of *Clostridium difficile* (ATCC9689), in a volume of 100 μl in Reinforced Clostridial broth medium, was added to the wells. The cultures were incubated at 37° C. for 48 hours in an anaerobic jar. The OD was read in a computer-controlled spectrophotometer (Thermomax) at a wavelength of 570 nm. The percentage growth inhibition achieved by the compounds was calculated according to standard methods and expressed as $IC_{90}$ (μg/ml) which defines the 90% inhibitory concentration for bacterial growth.

Results for D.1.1 and D.1.2

REP3123 displayed a good activity against both *C. perfringens* and *C. difficile* showing $IC_{90}$ of 0.25 and 0.5-1 μg/ml, respectively.

Compound (2) of the present invention displayed good activity against both *C. perfringens* and *C. difficile* showing $IC_{90}$ of 0.5 and 2 μg/ml, respectively.

D.1.3. In-vitro Method for Testing Compounds Against Several Bacteria

Flat-bottom, sterile 96-well plastic microtiter plates were filled with 100 μl of broth medium. Subsequently, stock solutions (100×final test concentration) of compounds were added in 2 μl volumes to a series of wells so as to allow evaluation of their effects on bacterial growth. Untreated control samples with and without inoculum were included in each microtiter plate. Approximately 50000 CFU per well of bacteria in a volume of 100 μl broth medium, was added to the wells. The plates were incubated at 37° C. Minimal inhibition concentration was determined as the highest concentration with no visible growth and expressed as $IC_{90}$ (μg/ml) which defines the 90% inhibitory concentration for bacterial growth.

Medium and Incubation Conditions:

*Staphylococcus aureus*, Methicillin-Resistant *Staphylococcus aureus, Staphylococcus epidermidis, Bacillus subtilis, Escherichia coli, Pseudomonas aeruginosa, Klebsiella pneumoniae, Listeria monocytogenes*: Mueller Hinton medium; incubation for 20-24 hours in aerobic conditions.

*Enterococcus faecalis, Streptococcus pneumonia*: Todd Hewitt medium; incubation for 20-24 hours in 5% $CO_2$.

*Mycobacterium smegmatis*: Mueller Hinton medium; incubation for 48 hours in aerobic conditions.

*Acinetobacter baumanii*: Nutrient broth; incubation for 20-24 hours in aerobic conditions

*Moraxella catarrhalis*: Brain heart Infusion medium; incubation for 20-24 hours in aerobic conditions.

Results for D.1.3:

Both REP3123 and compound (2) of the present invention did not display any activity against Gram negative bacteria. $IC_{90}$ of REP3123 were >32, >64, 16, >78 and >64 μg/ml against *E. coli, K. pneumoniae, M. cattarhalis, P. aeruginosa* and *A. baumanii*, respectively. $IC_{90}$ of compound (2) of the present invention were >31, >64, 16, >75 and >64 μg/ml against *E. coli, K. pneumoniae, M. cattarhalis, P. aeruginosa* and *A. baumanii*, respectively.

REP3123 displayed good activities against all the Gram positive bacteria tested. $IC_{90}$ of REP3123 were <0.25, <0.25, <0.25, <0.25, 1, 0.12 and 0.12 μg/ml against *S. aureus*, Methicillin-Resistant *S. aureus, S. epidermidis, E. faecalis, S. pneumonia, B. subtilis* and *L. monocytogenes*, respectively.

Compound (2) of the present invention was not active against all the Gram positive bacteria tested except for *E. faecalis* and *L. monocytogenes*. However, the activity of Compound (2) of the present invention was still much lower against these 2 microorganisms than that of REP3123. The $IC_{90}$ of Compound (2) of the present invention were 8-15, 7-13, 15, 1.5, >31, 4 and 2 μg/ml against *S. aureus*, Methicillin-Resistant *S. aureus, S. epidermidis, E. faecalis, S. pneumonia, B. subtilis* and *L. monocytogenes*, respectively.

Both REP3123 and compound (2) of the present invention did not display any activity against *Mycobacterium smegmatis*. The $IC_{90}$ of REP3123 and compound (2) of the present invention against *M. smegmatis* were 6-8 and >31 µg/ml, respectively.

TABLE 3 antibacterial activity of REP3123 and Compound (2) against Gram positive bacteria

| Gram positive bacteria | REP3123 | Compound (2) |
| --- | --- | --- |
| *S. aureus* | <0.25 µg/ml | 8-15 µg/ml |
| Methicillin-Resistant *S. aureus* | <0.25 µg/ml | 7-13 µg/ml |
| *S. epidermidis* | <0.25 µg/ml | 15 µg/ml |
| *E. faecalis* | <0.25 µg/ml | 1.5 µg/ml |
| *S. pneumonia* | 1 µg/ml | >31 µg/ml |
| *B. subtilis* | 0.12 µg/ml | 4 µg/ml |
| *L. monocytogenes* | 0.12 µg/ml | 2 µg/ml |

The comparison between REP3123 and Compound (2) of the present invention clearly demonstrates the broad-spectrum activity of REP3123 against Gram positive bacteria over the narrow-spectrum activity of Compound (2).

The invention claimed is:
1. A compound of formula (I)

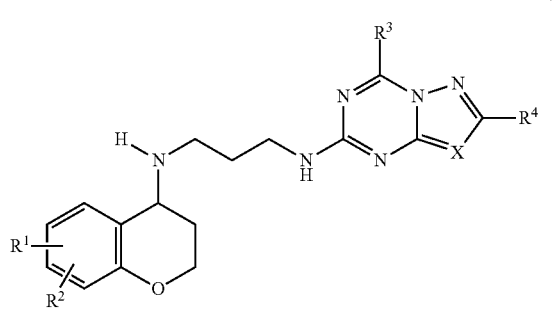

including any stereochemically isomeric form and tautomer thereof, wherein:
$R^1$ and $R^2$ are each independently selected from hydrogen, halo, hydroxy, $C_{1-6}$alkyl, polyhalo$C_{1-6}$alkyl, $C_{1-6}$alkyloxy, or polyhalo$C_{1-6}$alkyloxy;
$R^3$ is hydroxy, amino, mono- or di($C_{1-4}$alkyl)amino;
$R^4$ is hydrogen or $C_{1-4}$alkyl;
X is nitrogen or $CR^5$ wherein $R^5$ is hydrogen, halo or $C_{1-4}$alkyl;
provided that when $R^3$ is hydroxy then X is CH and $R^4$ is hydrogen;
or a pharmaceutically acceptable acid addition salt thereof, or a solvate thereof.

2. The compound of claim 1 or a pharmaceutically acceptable acid addition salt thereof, or a solvate thereof, having the (R)-configuration at the 4-position of the chromanyl moiety.

3. The compound of claim 2, or a pharmaceutically acceptable acid addition salt thereof, or a solvate thereof, wherein $R^1$ and $R^2$ are each halo.

4. The compound of claim 3, or a pharmaceutically acceptable acid addition salt thereof, or a solvate thereof, wherein $R^1$ and $R^2$ are each bromo and are located at the 6- and 8-position of the chromanyl moiety and wherein $R^3$ represents hydroxy.

5. The compound of claim 1, or a pharmaceutically acceptable acid addition salt thereof, or a solvate thereof, wherein $R^1$ and $R^2$ are each halo.

6. The compound of claim 1, or a pharmaceutically acceptable acid addition salt thereof, or a solvate thereof, wherein $R^1$ and $R^2$ are each bromo and are located at the 6- and 8-position of the chromanyl moiety.

7. The compound of claim 1, wherein the compound is:

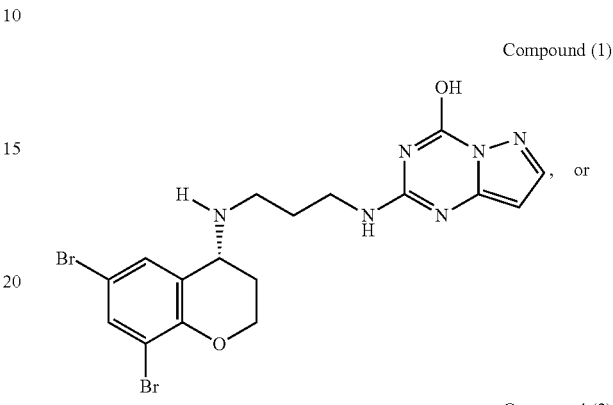

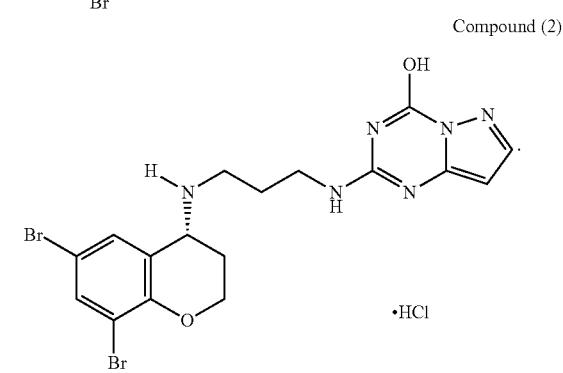

8. A pharmaceutical composition comprising a pharmaceutically acceptable carrier and a therapeutically active amount of a compound of claim 1, or a pharmaceutically acceptable acid addition salt thereof, or a solvate thereof.

9. A pharmaceutical composition comprising a pharmaceutically acceptable carrier and a therapeutically active amount of a compound of claim 7, or a pharmaceutically acceptable acid addition salt thereof, or a solvate thereof.

10. A method for treating a bacterial infection in a warm-blooded subject which comprises administering to the warm-blooded subject in need of such treatment a therapeutically effective amount of a compound of claim 1, or a pharmaceutically acceptable acid addition salt thereof, or a solvate thereof, wherein said bacterial infection is selected from a *Clostridium*, *S. aureus*, Methicillin-Resistant *S. aureus*, *S. epidermidis*, *E. faecalis*, *S. pneumonia*, *B. subtilis*, and *L. monocytogenes* bacterial infection.

11. The method of claim 10, wherein the bacterial infection is a *Clostridium* bacterial infection.

12. A method for treating a bacterial infection in a warm-blooded subject which comprises administering to the warm-blooded subject in need of such treatment a therapeutically effective amount of a compound of claim 7, or a pharmaceutically acceptable acid addition salt thereof, or a solvate thereof, wherein said bacterial infection is selected from a *Clostridium*, *S. aureus*, Methicillin-Resistant *S. aureus*, *S. epidermidis*, *E. faecalis*, *S. pneumonia*, *B. subtilis*, and *L. monocytogenes* bacterial infection.

13. The method of claim 12, wherein the bacterial infection is a *Clostridium* bacterial infection.

14. A process for preparing a compound of formula (I)

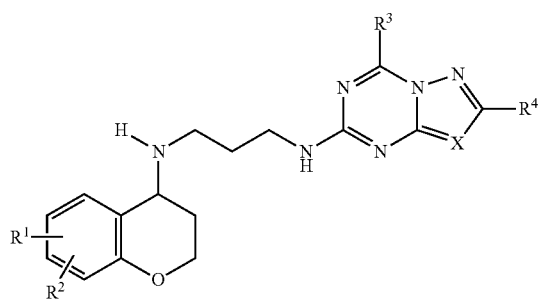

including any stereochemically isomeric form and tautomer thereof, or a pharmaceutically acceptable acid addition salt thereof, or a solvate thereof, comprising:

N-alkylating a compound of formula (II) with a compound of formula (III)

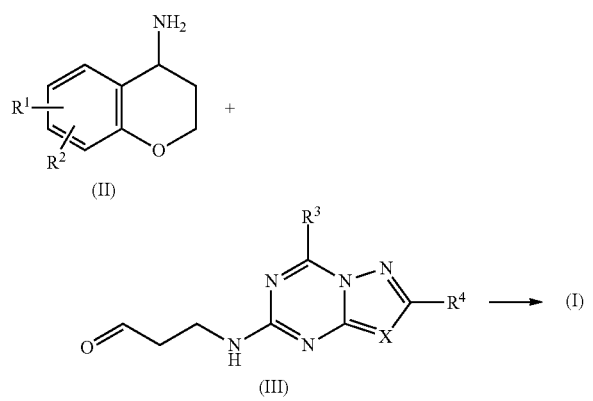

wherein $R^1$ and $R^2$ are each independently selected from hydrogen, halo, hydroxy, $C_{1-6}$alkyl, polyhalo$C_{1-6}$alkyl, $C_{1-6}$alkyloxy, or polyhalo$C_{1-6}$alkyloxy;

$R^3$ is hydroxy, amino, mono- or di($C_{1-4}$alkyl)amino;

$R^4$ is hydrogen or $C_{1-4}$alkyl;

X is nitrogen or $CR^5$ wherein $R^5$ is hydrogen, halo or $C_{1-4}$alkyl;

provided that when $R^3$ is hydroxy then X is CH and $R^4$ is hydrogen.

15. The process of claim 14, wherein said formula I compound is:

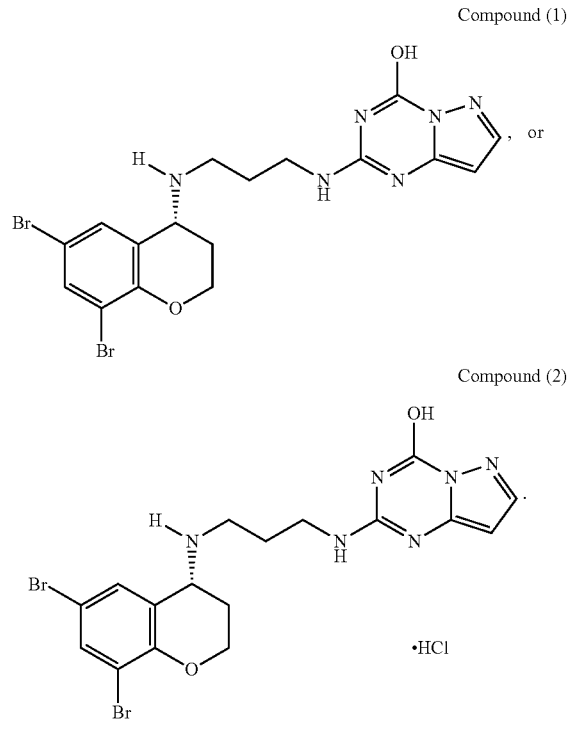 [SMILES: Oc1nc(NCCCN[C@@H]2CCOc3c(Br)cc(Br)cc32)nc2ccnn12 ; Oc1nc(NCCCN[C@@H]2CCOc3c(Br)cc(Br)cc32)nc2ccnn12 ; Cl]

* * * * *